(12) United States Patent
Young

(10) Patent No.: US 7,695,472 B2
(45) Date of Patent: Apr. 13, 2010

(54) LOCKING BONE PLATE

(75) Inventor: Robert Allan Young, Downingtown, PA (US)

(73) Assignee: Swiss Orthopedic Solutions SA, Morat (CH)

( * ) Notice: Subject to any disclaimer, the term of this patent is extended or adjusted under 35 U.S.C. 154(b) by 175 days.

(21) Appl. No.: 10/551,295

(22) PCT Filed: Mar. 26, 2004

(86) PCT No.: PCT/IB2004/000911

§ 371 (c)(1),
(2), (4) Date: Sep. 24, 2005

(87) PCT Pub. No.: WO2004/084701

PCT Pub. Date: Oct. 7, 2004

(65) Prior Publication Data

US 2006/0264946 A1    Nov. 23, 2006

Related U.S. Application Data

(60) Provisional application No. 60/457,786, filed on Mar. 26, 2003.

(51) Int. Cl.
*A61B 17/80* (2006.01)
*A61B 17/88* (2006.01)
*A61B 17/66* (2006.01)

(52) U.S. Cl. .................. 606/70; 606/71; 606/280; 606/289; 606/291; 606/286; 606/282

(58) Field of Classification Search ............ 606/69–71, 606/96, 280, 281, 282; 411/437, 84
See application file for complete search history.

(56) References Cited

U.S. PATENT DOCUMENTS

| | | | |
|---|---|---|---|
| 2,699,774 A | 1/1955 | Livingston | |
| 3,552,389 A | 1/1971 | Allgover et al. | |
| 3,659,595 A | 5/1972 | Haboush | |
| 3,716,050 A | 2/1973 | Johnston | |
| 3,779,240 A * | 12/1973 | Kondo | 606/282 |
| 3,824,995 A | 7/1974 | Getscher et al. | |
| 3,842,825 A | 10/1974 | Wagner | |

(Continued)

FOREIGN PATENT DOCUMENTS

DE    2806414 A1    10/1978

(Continued)

OTHER PUBLICATIONS

Brueckmann et al., Proximal Tibial Osteotomy, Orthopedic Clinics of North America, vol. 13, No. 1, (Jan. 1982), p. 3-16.
Sundaram et al., Dome Osteotomy of the Tibia for Osteoarthritis of the Knee, The Journal of Bone and Joint Surgery, vol. 68-B, No. 5, (Nov. 1986), p. 782-786.

(Continued)

*Primary Examiner*—Thomas C Barrett
*Assistant Examiner*—Matthew Lawson

(57) ABSTRACT

A bone plate with a longitudinal axis has a bone-contacting bottom side and a top side. Sets of overlapping holes communicate through the plate from the top to the bottom side. The overlapping holes have multifaceted surfaces such as a threaded surface or a coaxial series of annular grooves. The sets of overlapping holes are a adapted to receive a bone screw with a head and a bone-engaging thread.

34 Claims, 13 Drawing Sheets

U.S. PATENT DOCUMENTS

| | | | |
|---|---|---|---|
| 4,120,298 A | | 10/1978 | Fixel |
| 4,219,015 A | * | 8/1980 | Steinemann ............... 606/280 |
| 4,403,606 A | | 9/1983 | Woo et al. |
| 4,408,601 A | * | 10/1983 | Wenk ..................... 606/282 |
| 4,409,973 A | | 10/1983 | Neufeld |
| 4,421,112 A | | 12/1983 | Mains et al. |
| 4,454,876 A | | 6/1984 | Mears |
| 4,493,317 A | * | 1/1985 | Klaue ..................... 606/69 |
| 4,498,601 A | | 2/1985 | Fort |
| 4,501,268 A | | 2/1985 | Comparetto |
| 4,502,474 A | | 3/1985 | Comparetto |
| 4,509,511 A | | 4/1985 | Neufeld |
| 4,513,744 A | | 4/1985 | Klaue |
| 4,545,876 A | | 10/1985 | McGivern, Jr. |
| 4,565,191 A | | 1/1986 | Slocum |
| 4,565,193 A | | 1/1986 | Streli |
| 4,611,581 A | * | 9/1986 | Steffee ..................... 606/61 |
| 4,662,891 A | | 5/1987 | Noiles |
| 4,677,973 A | | 7/1987 | Slocum |
| 4,696,290 A | | 9/1987 | Steffee |
| 4,762,122 A | | 8/1988 | Slocum |
| 4,790,297 A | | 12/1988 | Luque |
| 4,794,918 A | * | 1/1989 | Wolter ..................... 606/69 |
| 4,800,874 A | | 1/1989 | David et al. |
| 4,867,144 A | | 9/1989 | Karas et al. |
| 4,875,475 A | | 10/1989 | Comte et al. |
| 4,957,479 A | | 9/1990 | Roemer |
| 4,957,496 A | | 9/1990 | Schmidt |
| 4,957,497 A | | 9/1990 | Hoogland et al. |
| 4,959,065 A | | 9/1990 | Arnett et al. |
| 4,988,350 A | | 1/1991 | Herzberg |
| 5,002,544 A | | 3/1991 | Klaue et al. |
| 5,006,120 A | | 4/1991 | Carter |
| 5,015,248 A | | 5/1991 | Burstein et al. |
| 5,041,113 A | * | 8/1991 | Biedermann et al. ........ 606/288 |
| 5,085,660 A | | 2/1992 | Lin |
| 5,087,260 A | | 2/1992 | Fixel |
| 5,176,679 A | | 1/1993 | Lin |
| 5,216,941 A | | 6/1993 | Kolvereid |
| 5,232,249 A | | 8/1993 | Kolvereid |
| 5,261,910 A | | 11/1993 | Warden et al. |
| 5,275,601 A | | 1/1994 | Gogolewski et al. |
| 5,304,180 A | | 4/1994 | Slocum |
| 5,324,290 A | | 6/1994 | Zdeblick et al. |
| 5,364,399 A | * | 11/1994 | Lowery et al. ............... 606/295 |
| 5,487,741 A | * | 1/1996 | Maruyama et al. ........... 606/60 |
| 5,601,553 A | * | 2/1997 | Trebing et al. ............... 606/61 |
| 5,681,311 A | | 10/1997 | Foley et al. |
| 5,709,686 A | * | 1/1998 | Talos et al. .................. 606/281 |
| 5,733,287 A | | 3/1998 | Tepic et al. |
| 5,741,258 A | | 4/1998 | Klaue et al. |
| 5,810,823 A | | 9/1998 | Klaue et al. |
| 5,851,207 A | * | 12/1998 | Cesarone .................... 606/69 |
| 5,968,047 A | | 10/1999 | Reed |
| 5,976,141 A | | 11/1999 | Haag et al. |
| 5,997,541 A | | 12/1999 | Schenk |
| 6,048,344 A | | 4/2000 | Schenk |
| 6,096,060 A | | 8/2000 | Fitts et al. |
| 6,206,881 B1 | | 3/2001 | Frigg et al. |
| 6,309,393 B1 | | 10/2001 | Tepic et al. |
| 6,331,179 B1 | * | 12/2001 | Freid et al. .................. 606/61 |
| 6,358,250 B1 | * | 3/2002 | Orbay ........................ 606/69 |
| 6,406,478 B1 | * | 6/2002 | Kuo ........................... 606/71 |
| 6,533,786 B1 | * | 3/2003 | Needham et al. ............ 606/282 |
| 6,623,486 B1 | * | 9/2003 | Weaver et al. ............... 606/69 |
| 6,706,046 B2 | | 3/2004 | Orbay et al. |
| 6,719,759 B2 | * | 4/2004 | Wagner et al. ............... 606/69 |
| 6,821,278 B2 | * | 11/2004 | Frigg et al. .................. 606/69 |
| 7,063,701 B2 | * | 6/2006 | Michelson ................... 606/73 |
| 7,090,676 B2 | | 8/2006 | Huebner et al. |
| 7,354,441 B2 | * | 4/2008 | Frigg ......................... 606/261 |
| 2002/0045901 A1 | | 4/2002 | Wagner et al. |
| 2002/0156474 A1 | * | 10/2002 | Wack et al. .................. 606/69 |
| 2002/0183752 A1 | | 12/2002 | Steiner et al. |
| 2003/0040748 A1 | | 2/2003 | Aikins et al. |
| 2004/0167522 A1 | * | 8/2004 | Niederberger et al. ........ 606/69 |
| 2004/0181228 A1 | | 9/2004 | Wagner et al. |
| 2005/0049594 A1 | * | 3/2005 | Wack et al. .................. 606/69 |
| 2005/0065524 A1 | * | 3/2005 | Orbay ........................ 606/69 |
| 2005/0080421 A1 | * | 4/2005 | Weaver et al. ............... 606/69 |
| 2005/0216008 A1 | | 9/2005 | Zwirnmann et al. |
| 2005/0216009 A1 | * | 9/2005 | Michelson ................... 606/69 |
| 2006/0212035 A1 | | 9/2006 | Wotton, III |

FOREIGN PATENT DOCUMENTS

| | | |
|---|---|---|
| DE | 0207884 | 3/1990 |
| DE | 43 41 980 | 6/1995 |
| DE | 4341980 | 6/1995 |
| DE | 4343117 | 6/1995 |
| EP | 0100114 | 2/1984 |
| EP | 0355035 | 2/1990 |
| FR | 2472373 | 7/1981 |
| FR | 2556583 | 12/1983 |
| FR | 2606268 | 5/1988 |
| WO | 0053110 | 9/2000 |
| WO | 0053111 | 9/2000 |
| WO | 0119267 | 3/2001 |
| WO | 0154601 | 8/2001 |
| WO | WO 01/54601 | 8/2001 |
| WO | 0200127 | 1/2002 |
| WO | 02096309 | 12/2002 |
| WO | WO 02/096309 | 12/2002 |
| WO | 2004089233 | 2/2004 |
| WO | 2005117732 | 12/2005 |
| WO | WO2005/117732 | 12/2005 |

OTHER PUBLICATIONS

Slocum et al, Tibial Plateau Leveling Osteotomy for Repair of Cranial Cruciate Ligament Rupture in the Canine, Veterinary Clinics of North America: Small Animal Practice, vol. 23, No. 4, (Jul. 1993), p. 777-795.

Reif et al, Effect of Tibial Plateau Leveling on Stability of the Canine Cranial Cruciate-Deficient Stifle Joint: An in Vitro Study, Veterinary Surgery, 31, (2002), p. 147-154.

Wheeler et al., In Vitro Effects of Osteotomy Angle and Osteotomy Reduction on Tibial Angulation and Rotation During the Tibial Plateau-Leveling Osteotomy Procedure, Veterinary Surgery, 32, (2003), p. 371-377.

Fettig et al., Observer Variability of Tibial Plateau Slope Measurement in 40 Dogs With Cranial Cruciate Ligament-Deficient Stifle Joints, Veterinary Surgery, 32, (2003), p. 471-478.

Miniaci et al., Proximal Tibial Osteotomy. A New Fixation Device, PubMed Article.

Lang et al., Cylindrical Osteotomy of the Upper End of the Tibia, PubMed Article.

Schneider et al., Cylindrical Osteotomy of the Upper Extremity of the Tibia with Advancement of the Patellar Ligament. Biomechanical Treatment of Gonarthrosis, PubMed Article.

Cassarino et al., High Domed Tibial Osteotomy in the Treatment of Angular Deviations of the Knee. A System of Surgical Instrumentation, PubMed Article.

Soccetti et al., Domed High Tibial Osteotomy: the Long-Term Results in Tibiofemoral Arthritis with and without Malalignment of the Extensor Apparatus, PubMed Article.

Slocum et al., Current Techniques in Small Animal Surgery, Baltimore: Williams & Wilkins, TX-4-606-643, (1997), 1340 pages.

Slocum et al., Dog Trot, VAu-91-980, (1985).

Sundaram et al., Dome osteotomy of the tibia for osteoarthritis of the knee, PubMed Article.

Axis Fixation System by Sofamor Danek, published Feb. 1997, entire document.

* cited by examiner

LOCKING BONE PLATE

CROSS-REFERENCE TO RELATED APPLICATION

This application is a 371 of application Serial No. PCT/IB04/00911 filed Mar. 26, 2004, which is a continuation of provisional application Ser. No. 60/457,786 filed Mar. 26, 2003.

BACKGROUND OF THE INVENTION

This invention relates to devices, implants and prostheses used in orthopedic surgery, and, more particularly, to bone plates used to reinforce fractured bones and thus promote healing.

A compressive screw system, also known as the DCS system, is a bone plate system that has been used in trauma surgery for many years. The procedures for use of this system are well documented by the AO Institute, an institute having as one of its goals, the promotion of new orthopedic surgical procedures. This system included a bone plate having slots communicating therethrough. A land in which the slot is wider at one end defines a stepped surface adjacent the portion of the slot that extends through the bone plate. The stepped surface is generally cut with a spherical endmill, thus creating a spherical stepped surface.

In a still further development, bone plates have been developed having individual threaded apertures and non-threaded apertures interspersed along the length of the plate. In this and other designs, the distance between holes has become a standard. Although an improvement over the inserts noted above, the locking positions are pre-defined, and only available in limited locations, which also reduce surgical flexibility. In another product variation, expandable, lockable inserts enter into the slots of a standard bone plate. When the bone screw passes through one of these inserts and is torqued down, the insert expands and locks the screw in place. However, this insert is locked in a secondary operation. This is not desirable because this requires more operating room time and adds complexity to the procedure. Further, the inserts must be added in the specific location before the plate is fixed to the bone and cannot be subsequently inserted. This limits the choice of placement during surgery if the need arises.

Also, the above insert design relies on a friction lock via contact between two surfaces. Friction locks are not reliable and come lose more easily than threaded locked holes. The result of such a design is inferior to that of the threaded plate and screw designs discussed below.

In U.S. Pat. No. 5,002,544 to Klaue et al, there is shown an osteosynthetic pressure plate having a cross-section transverse to the longitudinal axis of the plate at least one point being wider toward the upper surface than toward the lower surface and the plate having recesses in the lower surface so that upon application to a bone there is space between the bone and the plate. The cross-section between the screw holes is reduced, preferably to the extent that the resistance of the plate to bending in this area is less than in the area of the holes. Because of the reduced bend resistance between the holes, the plate can more easily be adapted to conform to the anatomy of the bone. Furthermore, this can be done without deformation of the holes, thus minimizing the resulting loss of fatigue strength and minimizing the misfit of the screw heads.

Further, U.S. Pat. No. 5,709,686 to Takos et al describes a bone plate that has recesses or reduced thickness portions on its sides, between threaded apertures. Although the purpose is not specifically described, these recesses appear to function to avoid warpage of the threaded portions when the bone plate is bent. However, when such a bone plate is fixed to a bone, these discontinuous recesses are exposed and may potentially come into contact with and potentially aggravate muscle tissue.

Still further, U.S. Pat. No. 5,733,287 to Tepic et al shows (in FIG. 4), a plate that has transverse cuts 13 and a longitudinal cut 14 on the lower surface 7 to reduce contact between the plate and bone. Due to the transverse undercuts 13, the cross-section 15 between the holes is already significantly reduced and therefore is not further decreased by an additional groove 10 on the upper surface 6 as in the embodiment according to FIG. 3. To avoid a cross-section that is too thin, the groove 10 on the upper surface 6 is made discontinuous in short segmental grooves 16 providing a smooth transition into and out of the holes 8.

In yet another solution, PCT application no. WO01/54601 combines the features of the DCS system discussed above with a locking screw. This design combines the features of the DCS system with a locking screw. Such a system is known as the combi-slot. In this design, the stepped surface of the slot is generally ramped or tapered so as to be deeper at one end than at another. This enables the positioning and selective fixing of the bone plate for compressing two bone fragments together with a preload created by wedging action. In this manner, the bones are placed in a position that the surgeon believes would best promote healing.

Further, this combi-hole includes two distinct overlapping portions in a single slot. One portion of the slot is suited to receive a standard bone screw, while the other portion of the slot is suited to receive a threaded peg oriented perpendicular to the top surface of the bone plate. Also, the combi-holes are generally oriented with the threaded portions being on the innermost end of the combination and the unthreaded portions oriented toward the ends of the bone plate. This improvement increased the flexibility of choice available to orthopedic surgeons using the device in that it was more likely that a hole would be present at a suitable anchoring point in the bone plate. Nevertheless, there are often trauma situations that are best served by the threaded portion being at the extreme ends of the bone plate and/or at various positions throughout the plate. In addition, sometimes there is no specific center of the facture—in such a situation, use of the combi-hole design is limited.

While patent application no. WO01/54601 has proven advantageous because screws can be locked to the plate, the presence of an unthreaded slot limits the users ability to have multiple orientations for the screw.

In a further development, the AO Institute has studied and proposed the use of endpegs which are rigidly fixed in the extreme ends of the bone plate. Such an arrangement has been shown to better resist the flexing of the bone than use of a bone screw alone. Flexing can otherwise loosen the connection between the bone plate and bone in other bone plate systems.

In another development, German patent DE 4341980 A1, published on Jun. 14, 1995, describes a bone plate 2 having an elongated slot 8 in which the sidewalls of the long sides of the slot are not parallel and are further provided with an internal thread 9. Corresponding bone screws 3 or inserts 6 have a head 5 with an external taper 4 and thus can be fixed into any point along the length, but to various depths of penetration. Therefore, the final configuration upon fixing is indeterminate and, due to the small amount of contact between the threads of the insert or screw and the slot, as well as the fact that the screw will be able to slide in one direction, the design does not appear to lend itself to reliable fixing.

U.S. Pat. No. 5,324,290 shows a complex bone plate having slots with countersunk circular recessed cut at intervals along the slot (a similar arrangement is shown in U.S. Pat. No. 4,696,290). It further shows the bone plate torqued against the bone so as to at least marginally, conform to the shape of the bone (see FIG. 2). Other patents of interest include U.S. Pat. Nos. 3,716,050, 3,659,595, 5,681,311, 5,261,910, and 5,364,399, all showing combinations of conventional slots and recesses which do not fully accommodate a bone screw having a threaded head.

In comparison with the combi-hole design and the friction locking design described above, what is needed is a bone plate that provides greater flexibility of choice to the surgeon. More specifically, what is needed is a bone plate that provides this choice of plate placement while reliably and permanently fixing the bone plate to the bone fragments, in any hole position.

What is needed is a bone plate that provides greater flexibility of choice to the surgeon, in a bone plate that has multiple orientations for the locking screw and thus, plate placement, while reliably and permanently fixing the bone plate to the bone fragments, in any hole position.

In addition, what is needed is a versatile bone plate having recesses which determine where the bone plate will bend, in order to avoid the threads in any holes to be bent or warped, while maintaining a smooth external surface.

Finally, what is needed is a bone plate with holes that create bi-directional compression.

SUMMARY OF THE INVENTION

A bone plate is provided having a longitudinal axis, a bone-contacting bottom side and a top side. Sets of overlapping holes communicate through the plate from the top to the bottom side. The overlapping holes have multifaceted surfaces such as a threaded surface or a coaxial series of annular grooves. The sets of overlapping holes are adapted to receive a bone screw with a head and a bone-engaging thread.

An object of the invention is to provide an orthopedic surgeon greater flexibity of choice in that a threaded peg providing secure fixing can be positioned at any interval along the bone plate, including at its extreme ends.

DETAILED DESCRIPTION OF THE PREFERRED EMBODIMENT

Figure 8:
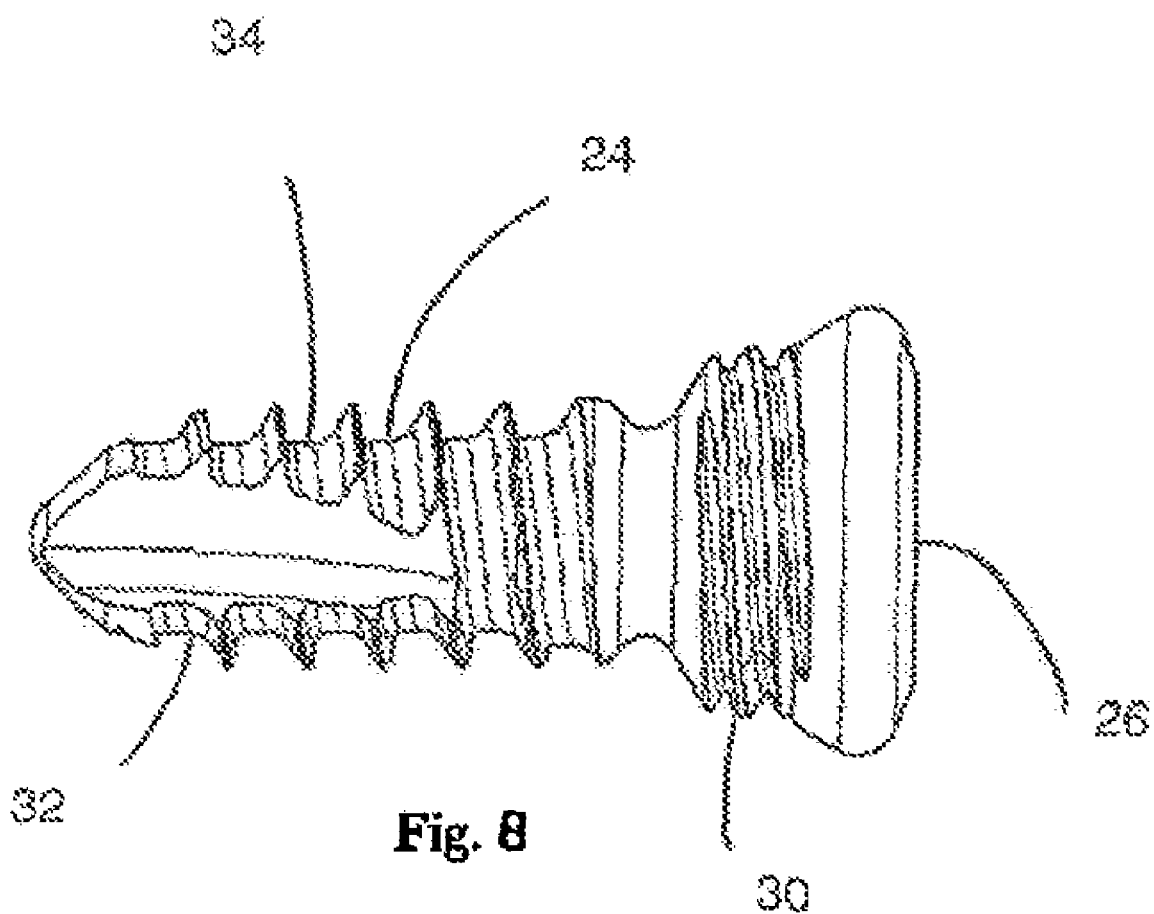
FIG. 8 is a side view of a bone screw having a head and a bone-engaging thread.

Referring now to FIGS. 1a to 1d, a bone plate 10 with a longitudinal axis 12 has a bone-contacting bottom side 14 and a top side 16. Multiple sets 20 of overlapping holes 22 communicate through the plate 10 from the top side 16 to the bottom side 14. The overlapping holes 22 are adapted to receive a bone screw 24 with a head 26 having a thread 30 and, on an opposite end 32, a body having a bone-engaging thread 34 (shown in FIG. 8). Sets 20 of two adjacent, overlapping holes 22 have an offset of a given distance d between centers 35 thereof. The offset defines a necked down portion 37 between the overlapping holes.

The multiple sets 20 of overlapping holes 22 allow for further adjustability and flexibility in positioning of the bone plate 10 during surgery. The overlapping holes 22 are formed normal to the top side 16 of the plate 10 (shown in FIGS. 1c and 1d).

Figure 1A:
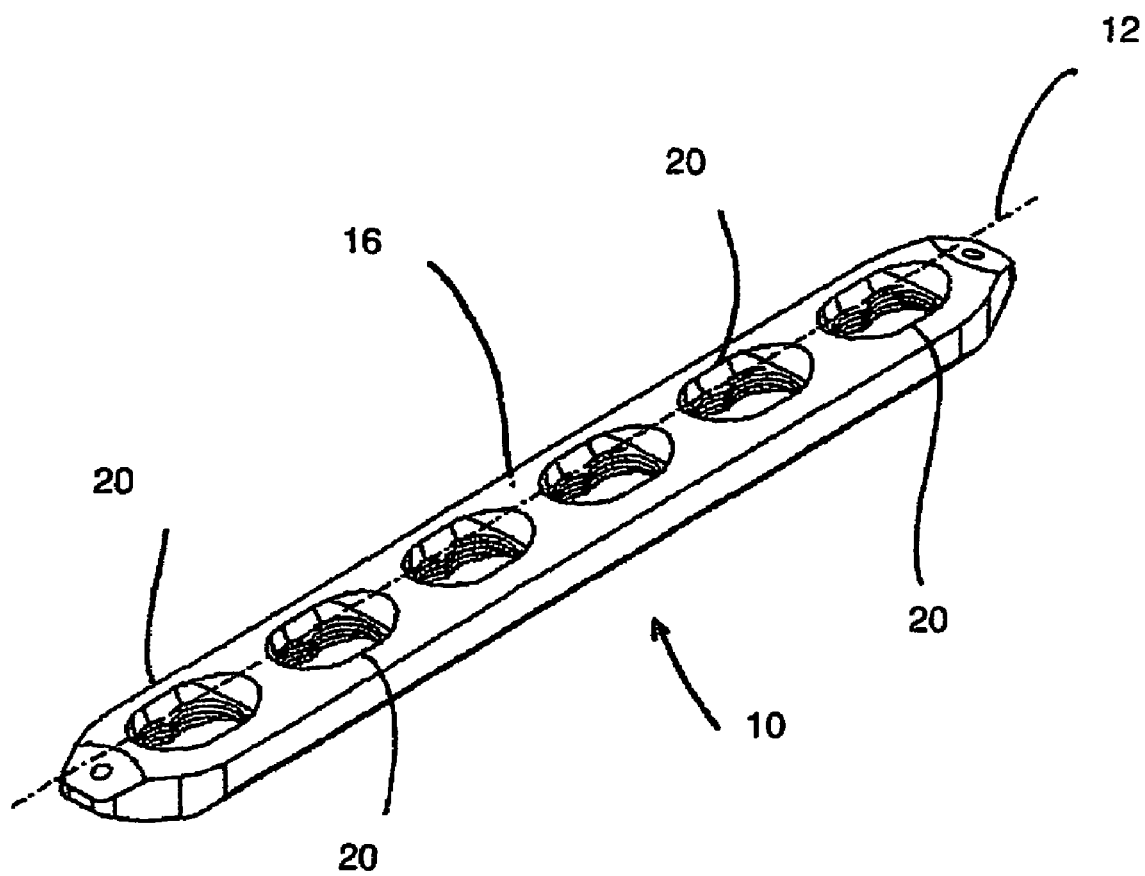
FIG. 1a is a perspective view of a bone plate in which the overlapping holes align along a longitudinal axis of the bone plate.
Figure 1B:
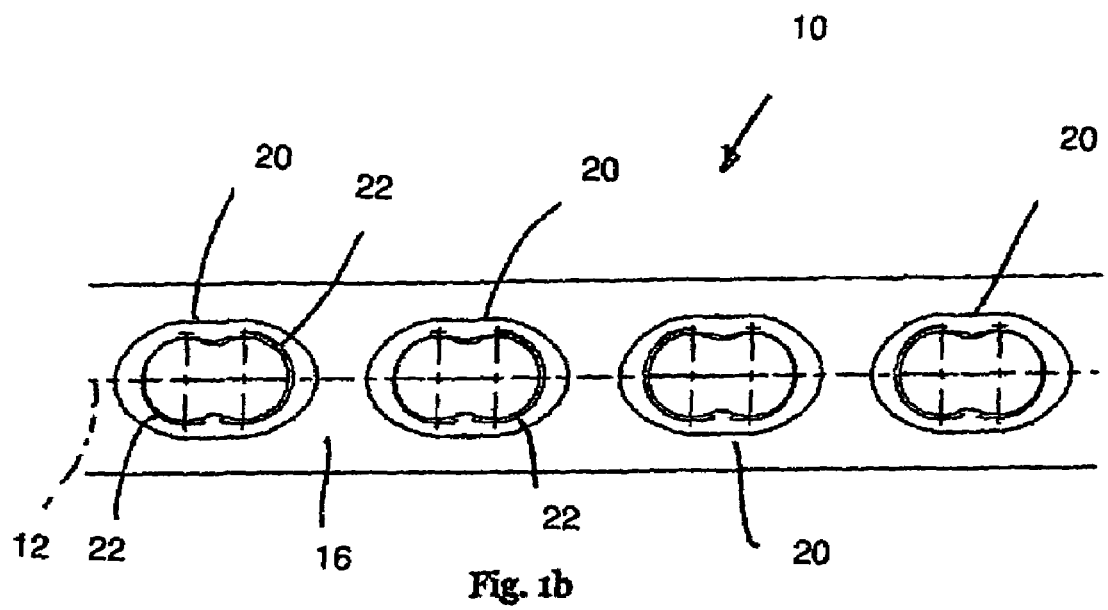
FIG. 1b is a top plan view of a bone plate in which the overlapping holes align along a longitudinal axis of the bone plate.
Figure 1C:
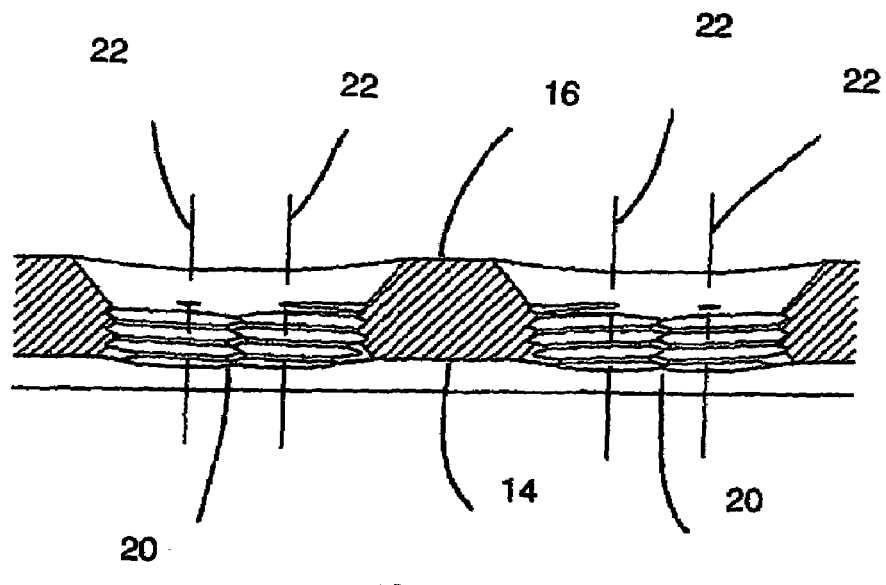
FIG. 1c is a longitudinal cross-sectional view of a bone plate in which the overlapping holes align along a longitudinal axis of the bone plate.
Figure 1D:
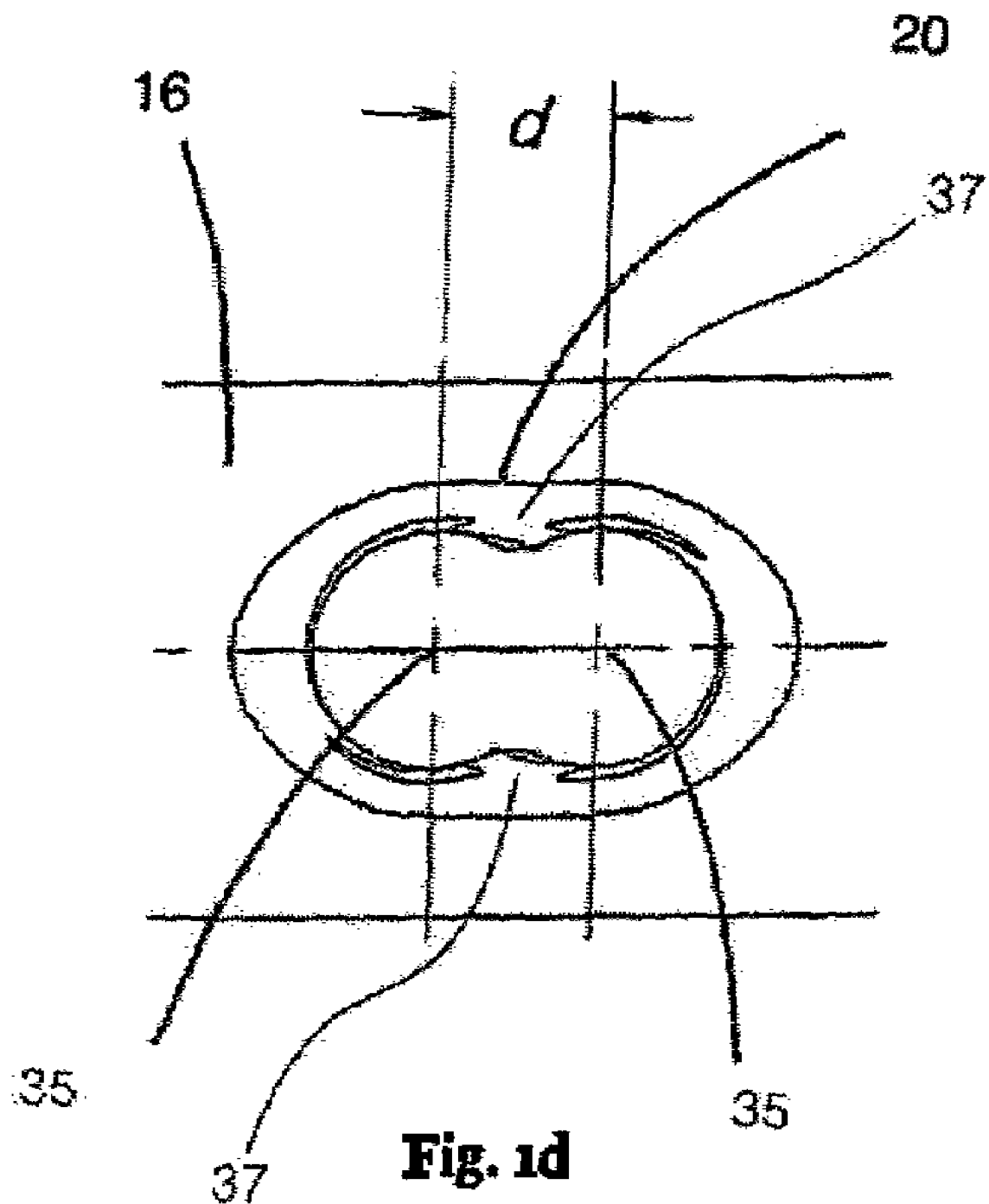
FIG. 1d is a top plan view of a single set of overlapping holes.
Figure 2A:
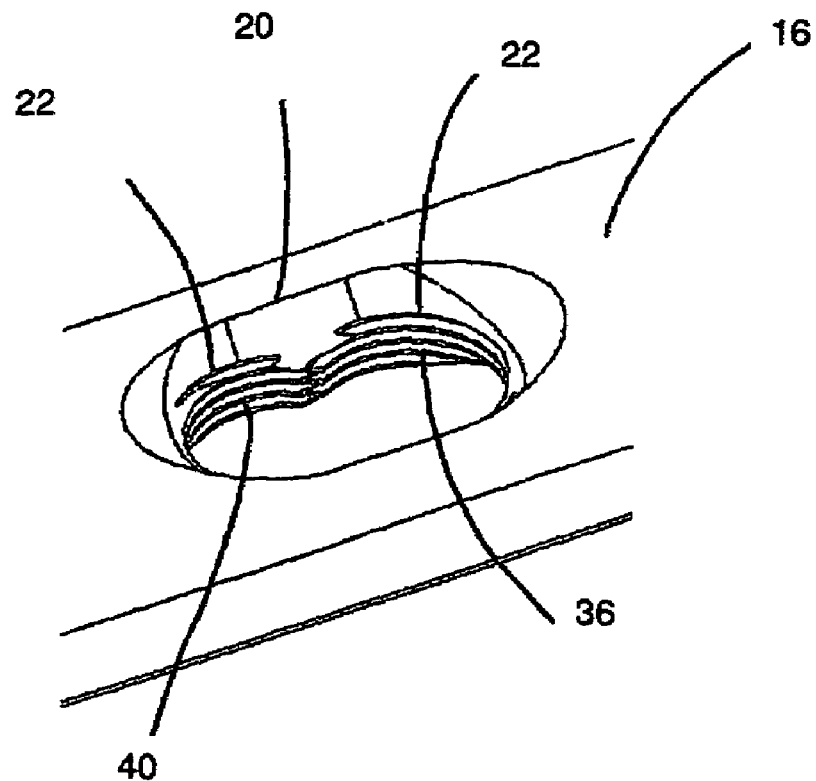
FIG. 2a is a perspective view of a set of two overlapping holes having a threaded surface.
Figure 2B:
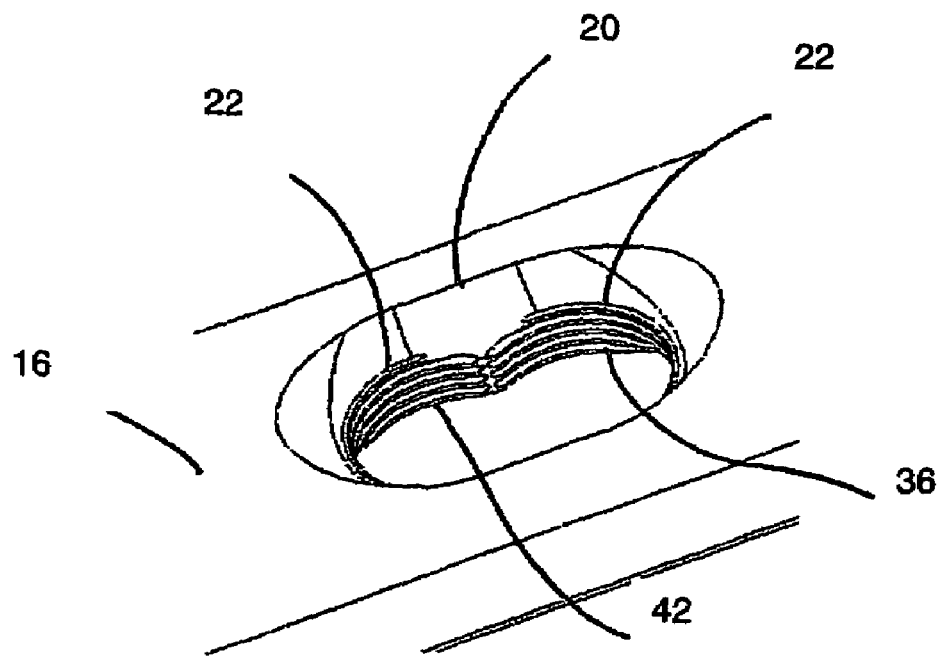
FIG. 2b is a perspective view of a set of two overlapping holes in which the surface of each hole is a coaxial series of annular grooves.

Referring now to FIGS. 2a and 2b, the overlapping holes 22 have multifaceted surfaces 36. In one embodiment, the multifaceted surface 36 is a threaded surface 40 (shown in FIG. 2a). In another embodiment, the multi-faceted surface 36 is a coaxial series of annular grooves 42 (shown in FIG. 2b).

Overlapping holes 22 are formed individually at an angle Ø offset from normal to the top side 16 of the plate 10. Such allows further flexibility of choice to the surgeon as to where and how to fasten the bone plate 10. Referring again to FIGS. 1c and 1d, where these overlapping holes 22 are oriented perpendicular to the top side 16 of the bone plate 10, he may chose to fasten the plates in a conventional manner, namely, perpendicular to the top side of the plate.

Figure 3:
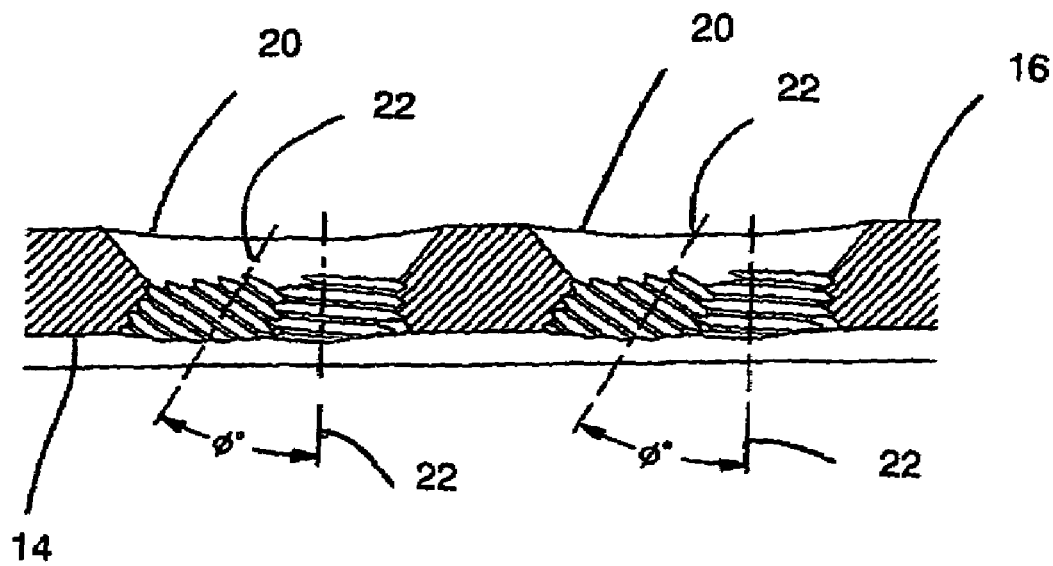
FIG. 3 is a longitudinal cross-section view in which some of the overlapping holes are formed normal to the top side of the plate.

Referring now to FIG. 3, in a preferred embodiment, some of the overlapping holes 22 are formed normal to the top side 16 of the plate 10.

Figure 4:
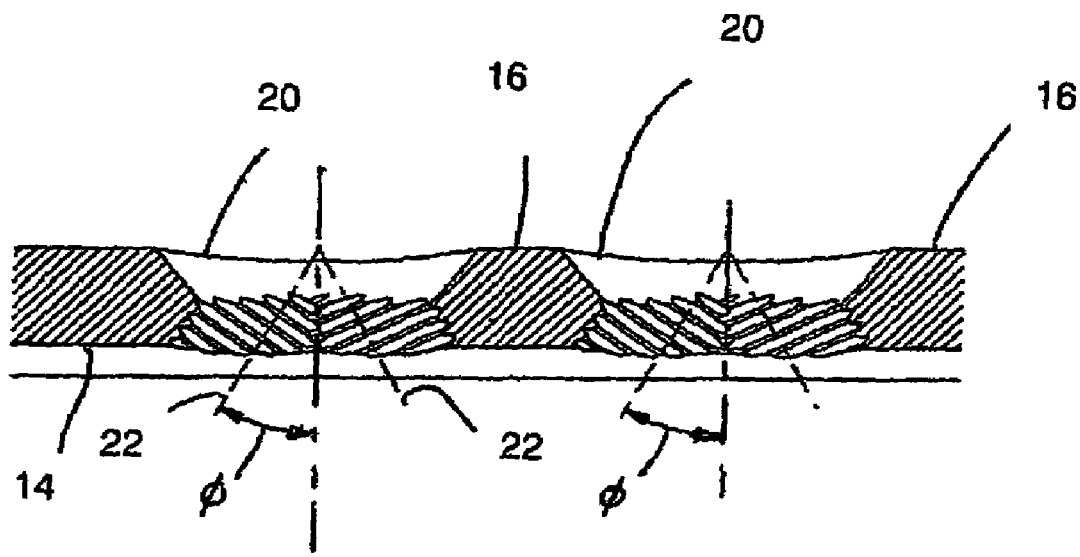
FIG. 4 is a longitudinal cross-sectional view in which all the overlapping holes are formed at an angle offset from normal to the top side of the plate.

Alternatively, as shown in FIG. 4, all of the overlapping holes 22 are formed at an angle Ø offset from normal to the top side 16 of the plate 10.

Figure 5:
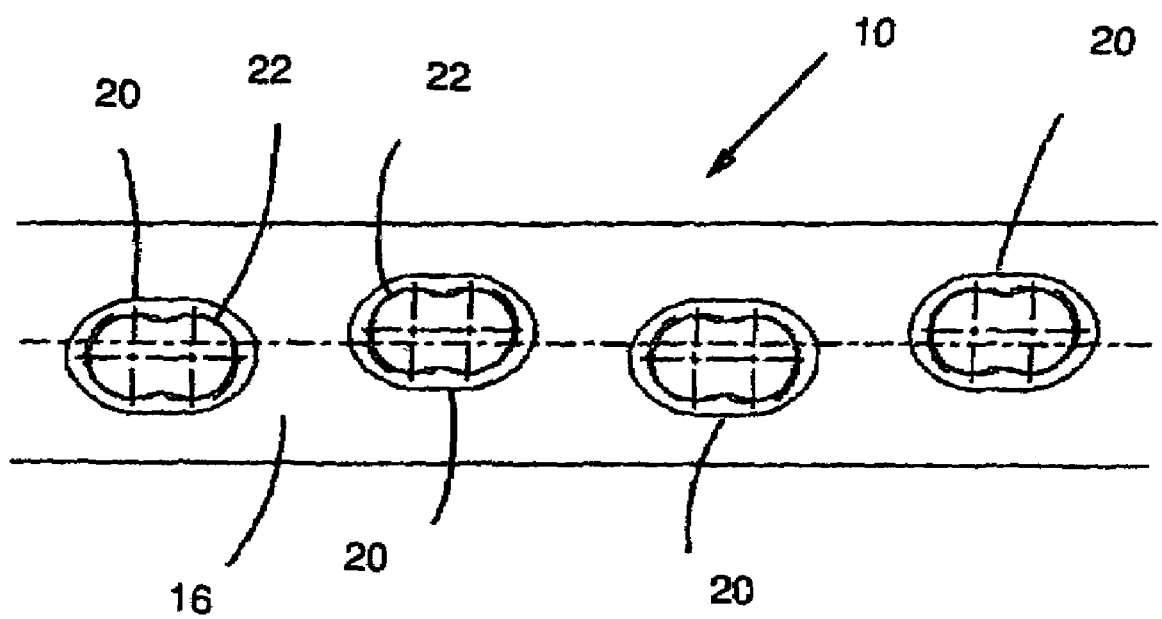
FIG. 5 is a top plan view of a bone plate in which the overlapping holes are staggered along a longitudinal axis of the bone plate.

Referring now to FIG. 5, the overlapping holes 22 may be formed offset from the longitudinal axis 12 of the bone plate 10, in a staggered manner.

Figure 6A:
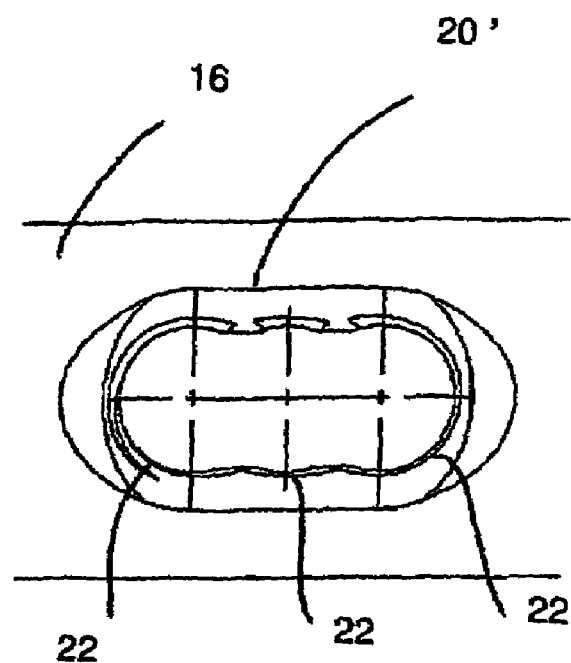
FIG. 6a is a top plan view of the bone plate showing a set of three overlapping holes.
Figure 6B:
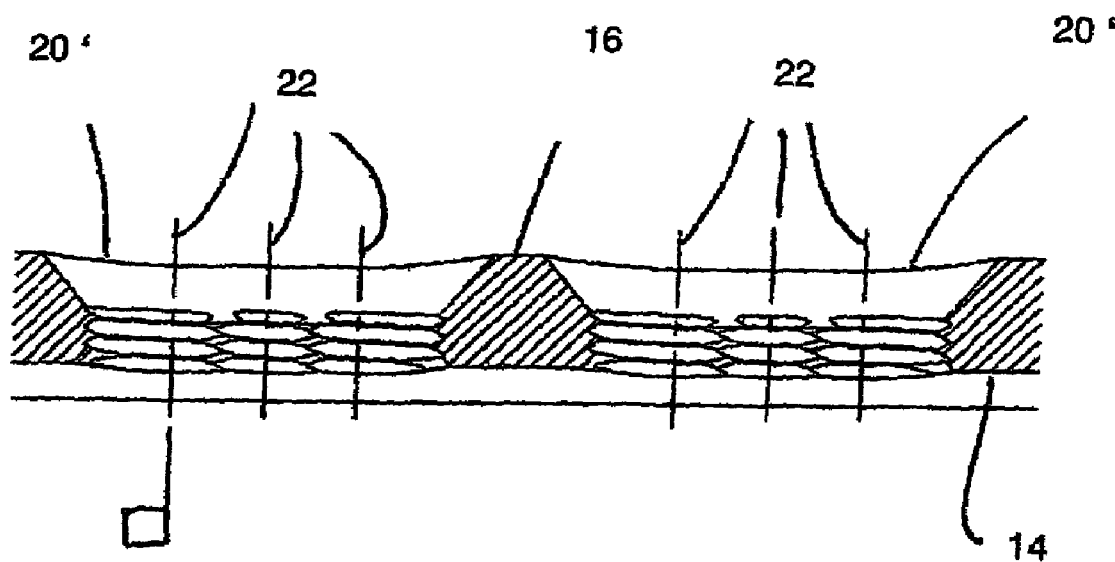
FIG. 6b is a longitudinal cross-sectional view showing the sets of tree overlapping holes in which all holes are aligned normal to the top surface of the bone plate.

Referring now to FIGS. 6a to 6d, in an alternate embodiment, the bone plate 10 may include sets 20 of three overlapping holes 22. Referring in particular to FIG. 6b, where these overlapping holes 22 are oriented perpendicularly to the top side 16 of the bone plate 10, the surgeon may chose to fasten the plates in a conventional manner.

Figure 6D:
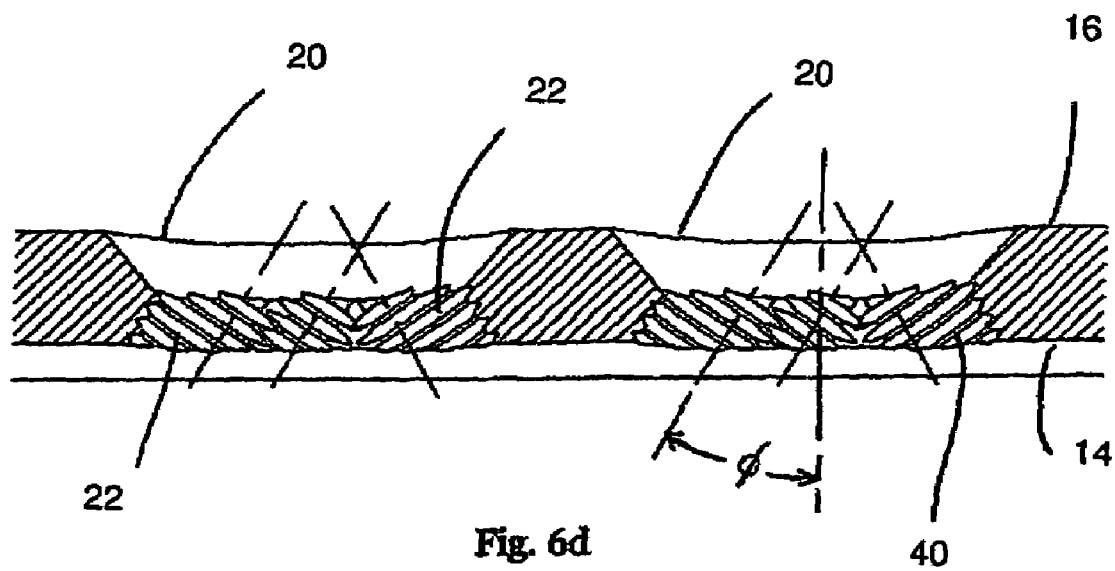
FIG. 6d is a longitudinal cross-sectional view showing the sets of three overlapping holes in which all holes are aligned at an angle offset from normal to the top surface of the bone plate.
Figure 6C:
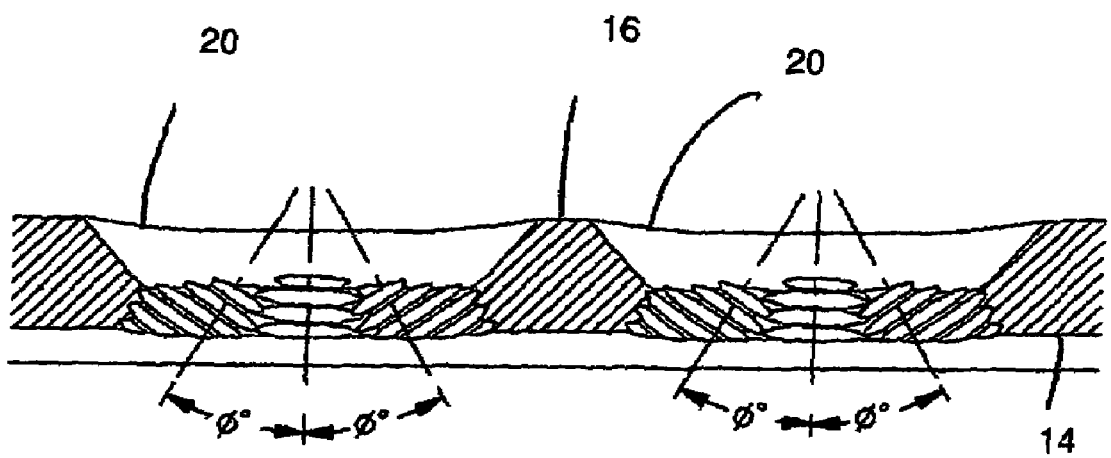
FIG. 6c is a longitudinal cross-sectional view showing the sets of three overlapping holes in which some of the holes are aligned normal to the top surface of the bone plate.

Referring in particular to FIG. 6c, in a preferred embodiment, some of the overlapping holes 22 are formed normal to the top side 16 of the plate 10.

Alternatively, as shown in FIG. 6d, all of the overlapping holes 22 are formed at an angle Ø offset from normal to the top side 16 of the plate 10.

Figure 7A:
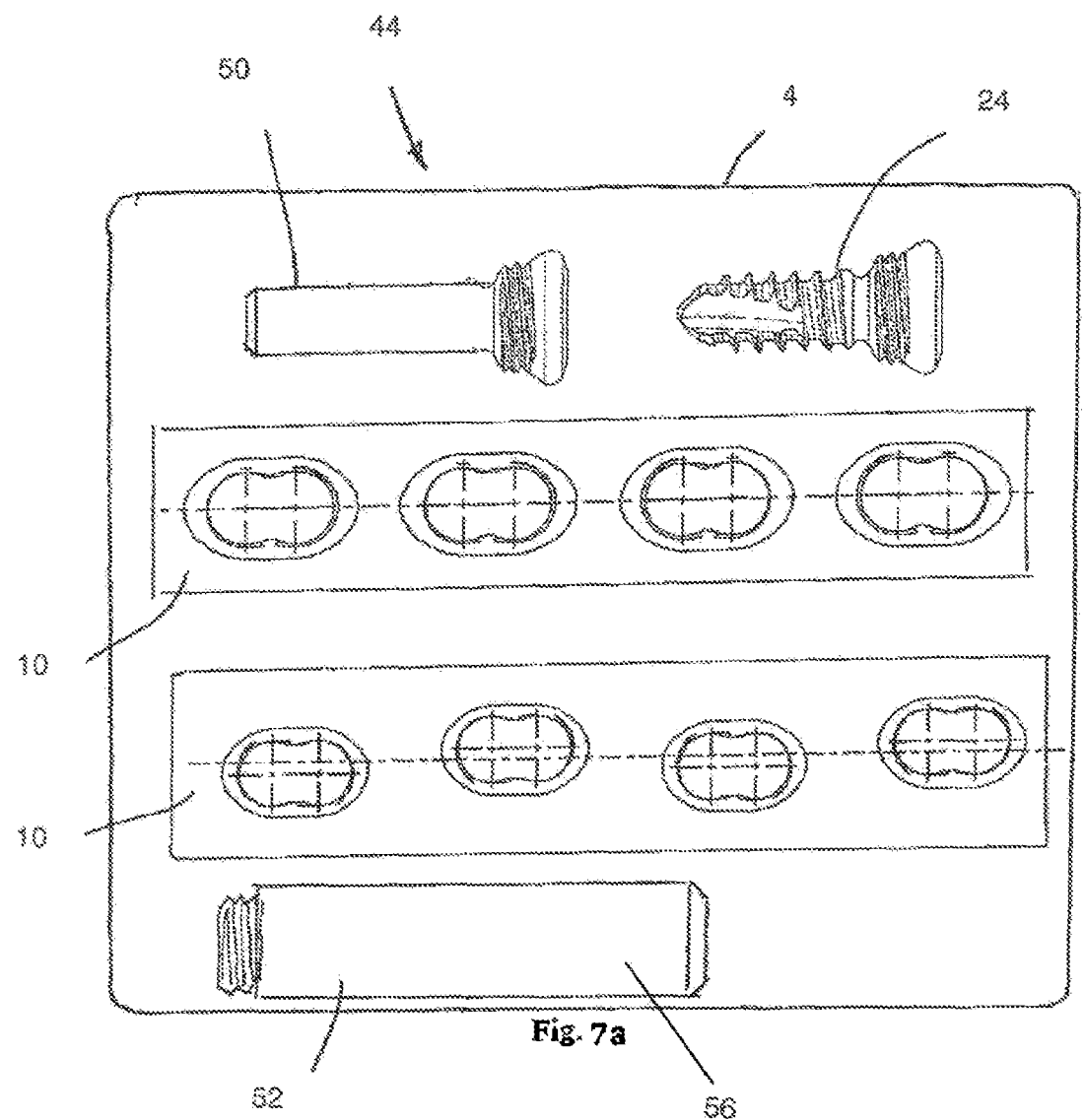
FIG. 7a is a plan view of an orthopedic kit of the invention including a case, a bone plate, a variety of bone screws, and threaded pegs of various lengths.
Figure 7B:
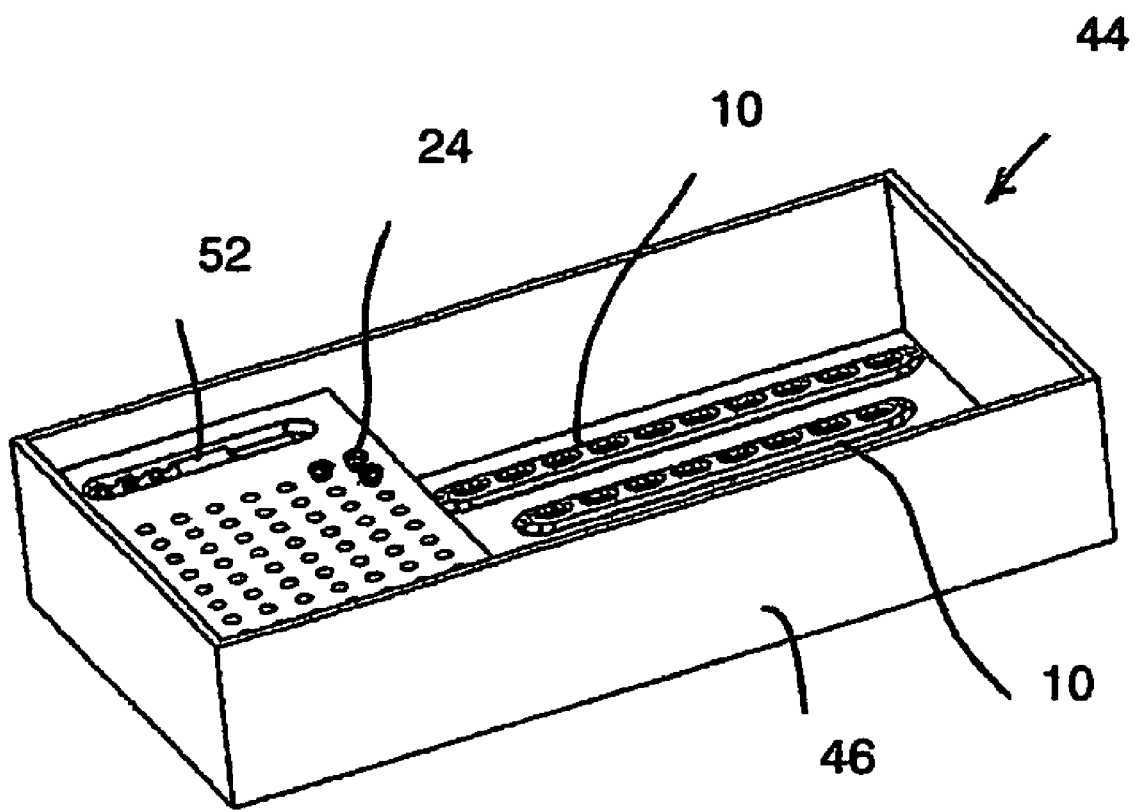
FIG. 7b is a perspective view of an orthopedic kit of the invention including a case, a bone plate, a variety of bone screws, and a drill guide.

Referring now to FIGS. 7a and 7b, in another embodiment, orthopedic kits 44 are provided which include a case 46, a bone plate 10, a variety of bone screws 24, threaded pegs 50 of various lengths, and a drill guide 52. The drill guide 52 has a threaded end 54 that threads into the thread 40 of an overlapping hole 22. The drill guide 52 has a main drill guide surface 56 to securely hold the drill guide in a desired orientation with respect to the bone plate 10 in order to stabilize a drill (not shown) used in an orthopedic procedure.

Figure 9A:
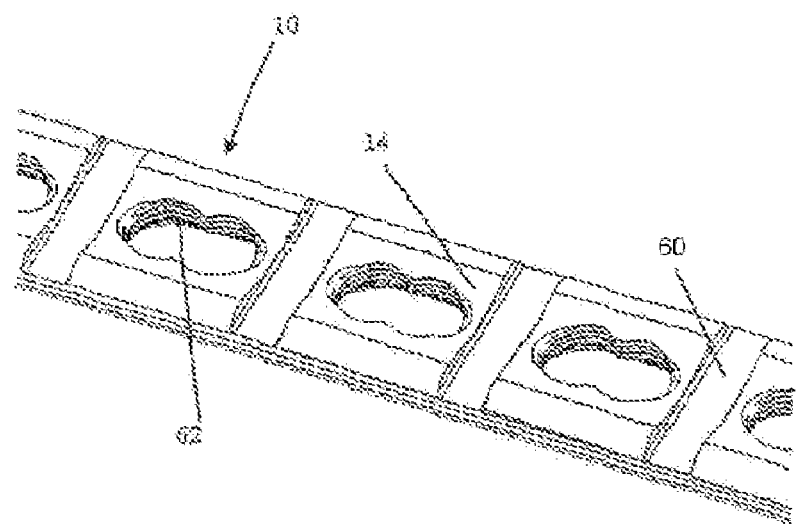
FIG. 9a is a perspective view of an alternate embodiment of the bone plate having lower recesses.
Figure 9B:
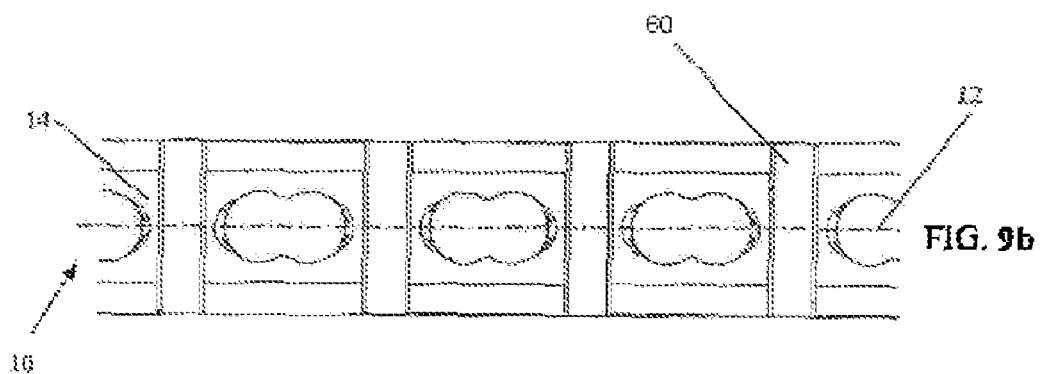
FIG. 9b is a second perspective view of the alternate embodiment of the bone plate.
Figure 9C:
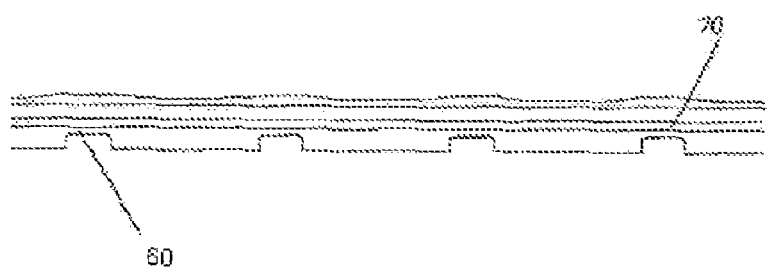
FIG. 9c is a side view of the alternate embodiment of the bone plate.

Referring now to FIGS. 9a-9c, an alternate embodiment of the bone plate 10' is provided with lower recesses 60 of rectangular form, extending transversely across the bone plate. These recesses 60 are preferably positioned at regular intervals along the longitudinal axis, between threaded apertures 62. Such recesses 60 are provided in order to reduce the contact area between the bottom side 14 of the bone plate 10' and the bone, as well as to prevent bending of the bone plate across a threaded aperture 62 (thus preventing warping of the threads 36). The total area removed from the bottom side 14 due to the recesses 60 is preferably less than or equal to 25% of the total surface area of the bottom side.

The recesses 60 are substantially located exclusively on the bottom side 14 and are sized so as to define a cross-section 64 transverse to the longitudinal axis and across the recesses. This ensures that a yield strength in bending across the recesses 60 is less than across a threaded aperture 62 and thus, prevents damage of the threads upon forming of the bone plate to mate with a curvilinear surface of a bone.

Figure 10A:
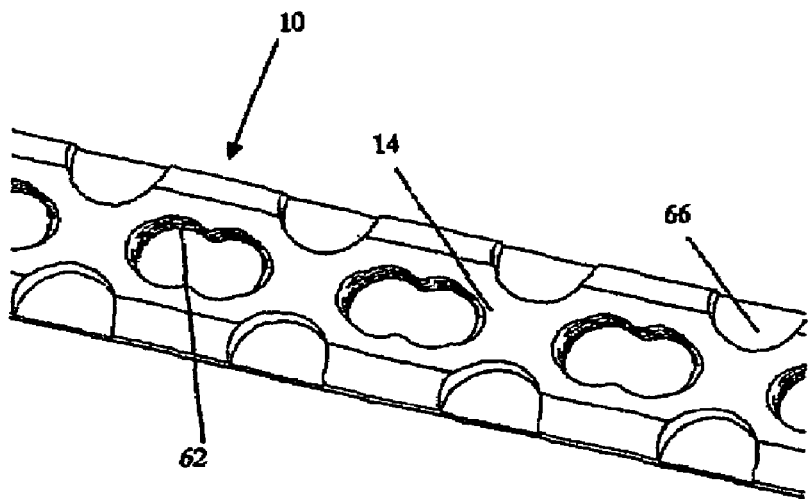
FIG. 10a is a perspective view of a second alternate embodiment showing lower recesses on the bone plate.
Figure 10B:
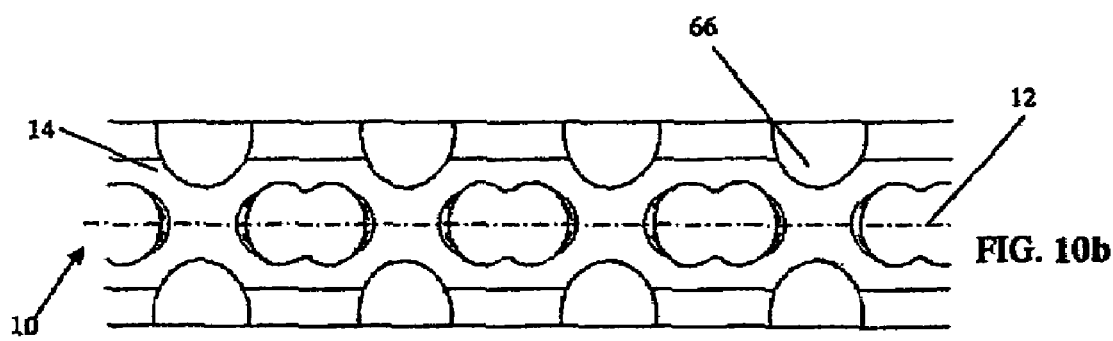
FIG. 10b is a bottom view of the alternate embodiment of the bone plate.
Figure 10C:
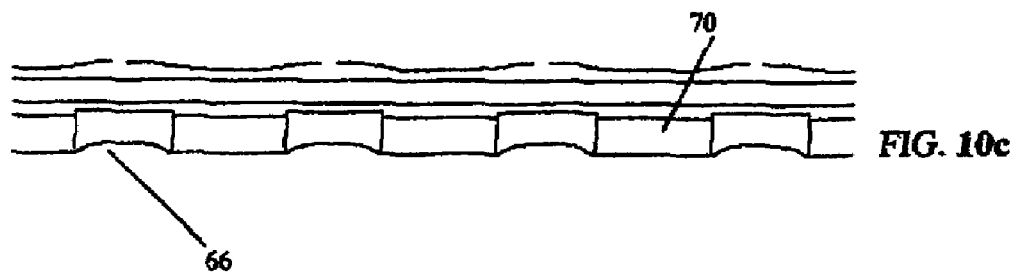
FIG. 10c is a side view of the alternate embodiment of the bone plate.

Referring now to FIGS. 10a-10c, a second alternate embodiment of the bone plate 10" is shown having another form of lower recesses 66. These recesses 66 do not extend across the bottom side 14 of the bone plate 10", but rather extend from a side 70 of the bone plate a short distance toward the centerline 12 of the bone plate, but do not traverse the centerline.

Note that the threaded apertures 62 used in the invention provide hole centers located at specific locations (as opposed to apertures that are formed as a slot). Use of threads centered at a specific point allows tile bone screw to be fixed at a specific location at which the surgeon may judge the bone structure to be best suited to support such a bone screw. Unlike designs using a slot, the apertures 62 of the invention eliminate wander of the screw in the aperture. This further permits placement at specific locations for buttressing and/or secure fixing in neutral screw loading areas.

In another feature, locking bone pegs (not shown) interface with the threaded apertures. The threads cut in the head of these pegs are designed so as to lock with the threaded apertures in order to better ensure rigid fixing of a fixture when using pegs having a body without threads. The locking feature used can be any of the known methods of locking threads by mechanical means.

In an advantage of the invention, the bone plate 10 provides greater flexibility of choice to the surgeon in that a threaded peg providing secure fixing can be positioned at any interval along the bone plate, including at its extreme ends.

In another advantage, the bone plate 10 provides greater flexibility of choice by providing multiple overlapping holes 22 oriented (1) along the longitudinal axis 12 of the bone plate, (2) oriented at an angle Ø to the longitudinal axis, and (3) staggered along the axis.

In still another advantage, the threaded apertures 40 of the bone plate 10 are provided with threads cut perpendicular to the top side 16 of the bone plate, as well as at an angle Ø to normal.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A bone plate having a thickness extending from a bone-contacting bottom side to a top side with at least one complex aperture extending through the plate thickness and comprised of at least two overlapping holes having an offset of a given distance between centers thereof, wherein any two immediately adjacent overlapping holes comprise a compression ramp extending from an oval shaped opening at the top side of the plate downwardly and inwardly part way through the plate thickness to a threaded lower portion having an hourglass shape extending from where the compression ramp ends at the hourglass shape to the bottom side of the bone plate with threaded surfaces of the overlapping holes meeting each other at a threaded overlap forming the hourglass shape, wherein the threaded lower portion is adapted to lock with threads of a corresponding bone screw in one or the other of the overlapping holes.

2. The bone plate of claim 1, wherein the overlapping holes are formed normal to the top side of the plate.

3. The bone plate of claim 1, wherein the overlapping holes are formed at an angle offset from normal to the top side of the plate.

4. The bone plate of claim 1, wherein at least one of the overlapping holes is formed normal to the top side of the plate and at least a second of the overlapping holes is formed at an angle offset from normal to the top side of the plate.

5. The bone plate of claim 1, wherein the complex aperture further comprises multiple sets of overlapping holes.

6. The bone plate of claim 5, wherein the overlapping holes are formed normal to the top side of the plate.

7. The bone plate of claim 5, wherein at least one of the overlapping holes is formed at an angle offset from normal to the top side of the plate.

8. The bone plate of claim 5, wherein at least one of the overlapping holes is formed normal to the top side of the plate and at least a second of the overlapping holes is formed at an angle offset from normal to the top side of the plate.

9. The bone plate of claim 5, wherein the multiple sets of overlapping holes are aligned along a longitudinal axis.

10. The bone plate of claim 5, wherein the multiple sets of overlapping holes are positioned in a staggered arrangement offset from a longitudinal axis of the bone plate.

11. The bone plate of claim 10, wherein the overlapping holes are formed normal to the top side of the plate.

12. The bone plate of claim 10, wherein at least one of the overlapping holes is formed at an angle offset from normal to the top side of the plate.

13. The bone plate of claim 10, wherein at least one of the overlapping holes is formed normal to the top side of the plate and at least a second of the overlapping holes is formed at an angle offset from normal to the top side of the plate.

14. The bone plate of claim 1, wherein the at least two overlapping holes are adapted to receive a bone screw with a head and a bone-engaging thread.

15. An orthopedic kit including:
a) a bone plate according to claim 1; and
b) at least one bone screw engageable with the bone plate.

16. The bone plate of claim 14, wherein the at least two overlapping holes are formed normal to the top side of the plate.

17. The bone plate of claim 14, wherein at least one of the at least two overlapping holes is formed at an angle offset from normal to the top side of the plate.

18. The bone plate of claim 14, wherein at least one of the overlapping holes is formed normal to the top side of the plate and at least a second of the overlapping holes is formed at an angle offset from normal to the top side of the plate.

19. The bone plate of claim 1, wherein the complex aperture is comprised of three overlapping holes.

20. The bone plate of claim 19, wherein the overlapping holes are formed normal to the top side of the plate.

21. The bone plate of claim 19, wherein at least one of the overlapping holes is formed at an angle offset from normal to the top side of the plate.

22. The bone plate of claim 19, wherein at least one of the overlapping holes is formed normal to the top side of the plate and at least a second of the overlapping holes is formed at an angle offset from normal to the top side of the plate.

23. The kit of claim 15, wherein a head of the bone screw has a plate engaging thread.

24. The kit of claim 15, further comprising a drill guide having a main drill guide surface and opposite end portions, one end portion of which is securely engageable with the threaded surface of the lower portion of each overlapping hole in the bone plate so as to securely hold the drill guide in a desired orientation with respect to the bone plate for stabilizing a drill used in an orthopedic procedure.

25. A bone plate with a longitudinal axis, a bone-contacting bottom side having a total surface area and a top side with at least one complex aperture extending through the plate thickness and comprised of at least two overlapping holes having an offset of a given distance between centers thereof, wherein any two immediately adjacent overlapping holes comprise a compression ramp extending from an oval shaped opening at the top side of the plate downwardly and inwardly part way through the plate thickness to a threaded lower portion having an hourglass shape extending from where the upper portion ends at the hourglass shape to the bottom side of the bone plate with threaded surfaces of the overlapping holes meeting each other at a threaded overlap forming the hourglass shape, the lower portion being adapted to lock with threads of a corresponding bone screw in one or the other of the overlapping holes, and wherein the bottom side includes recesses located between adjacent complex apertures and which are substantially located exclusively on the bottom side, the recesses being sized so as to define a cross-section transverse to the longitudinal axis and across the recesses that ensures that a yield strength in bending across the recesses is less than across a threaded aperture.

26. The bone plate of claim 25, wherein the recesses are substantially rectangular in form.

27. The bone plate of claim 25, wherein the recesses are equally spaced along the longitudinal axis.

28. The bone plate of claim 25, wherein a total area removed from the bottom side due to the recesses is less than or equal to 50% of the total surface area of the bottom side.

29. The bone plate of claim 25, wherein the recesses are transverse and extend across the width of the bone plate.

30. The bone plate of claim 25, wherein the recesses extend from a side of the bone plate transversely toward the longitudinal axis but do not cross the axis.

31. The bone plate of claim 1 wherein the threaded surface is a multi-faceted surface.

32. A bone plate having a thickness extending from a bone contacting bottom side to a top side with at least two complex apertures extending through the plate thickness, each complex aperture comprised of at least two overlapping holes having an offset of a given distance between centers thereof, wherein any two immediately adjacent overlapping holes comprise a compression ramp extending from an oval shaped opening at the top side of the plate downwardly and inwardly part way through the plate thickness to a threaded lower portion having an hourglass shape extending from where the upper portion ends at the hourglass shape to the bottom side of the bone plate with threaded surfaces of the overlapping holes meeting each other at a threaded overlap forming the hourglass shape, the lower portion being adapted to lock with threads of a corresponding bone screw in one or the other of the overlapping holes.

33. A bone plate having a longitudinal axis and a thickness extending from a bone-contacting bottom side to a top side with at least one complex aperture extending through the plate thickness and comprised of at least two overlapping holes having an offset of a given distance between centers thereof, wherein any two immediately adjacent overlapping holes comprise a compression ramp extending from an oval shaped opening at the top side of the plate downwardly and inwardly part way through the plate thickness to a threaded lower portion having an hourglass shape extending from where the upper portion ends at the hourglass shape to the bottom side of the bone plate with threaded surfaces of the overlapping holes meeting each other at a threaded overlap forming the hourglass shape, the lower portion being adapted to lock with threads of a corresponding bone screw in one or the other of the overlapping holes, and wherein the overlapping holes further having centers offset from the longitudinal axis of the plate.

34. A bone plate having a thickness extending from a bone-contacting bottom side to a top side with at least one complex aperture extending through the plate thickness, wherein the complex aperture is comprised of a compression ramp having an oval shape at the top side of the plate with the compression ramp extending from the top side downwardly and inwardly part way through the plate thickness to a lower portion having an hourglass shape extending through the bottom side and formed by two immediately adjacent threaded holes meeting each other at a threaded overlap with an offset of a given distance between centers of the overlapping holes.

* * * * *